(12) United States Patent
Burgess et al.

(10) Patent No.: US 8,764,731 B2
(45) Date of Patent: Jul. 1, 2014

(54) CONNECTOR FOR FLUID CONDUIT WITH INTEGRATED LUER ACCESS PORT

(75) Inventors: James E. Burgess, Mundelein, IL (US); John H. Kutsch, Harvard, IL (US)

(73) Assignee: Medline Industries, Inc., Mundelein, IL (US)

( * ) Notice: Subject to any disclaimer, the term of this patent is extended or adjusted under 35 U.S.C. 154(b) by 450 days.

(21) Appl. No.: 12/572,708

(22) Filed: Oct. 2, 2009

(65) Prior Publication Data
US 2011/0082431 A1    Apr. 7, 2011

(51) Int. Cl.
*A61M 25/16* (2006.01)
*A61M 25/18* (2006.01)

(52) U.S. Cl.
USPC .......................................... 604/539

(58) Field of Classification Search
USPC .......................... 604/533, 538, 539
See application file for complete search history.

(56) References Cited

U.S. PATENT DOCUMENTS

| | | | |
|---|---|---|---|
| 2,538,662 A | 1/1951 | Abbott | |
| D252,470 S | 7/1979 | Pawlak | |
| D259,278 S | 5/1981 | McCaw et al. | |
| D283,725 S | 5/1986 | Mahoney | |
| D300,361 S | 3/1989 | Tokarz | |
| 5,033,476 A * | 7/1991 | Kasai | 600/577 |
| 5,135,492 A * | 8/1992 | Melker et al. | 604/508 |
| D342,135 S | 12/1993 | Goldberger et al. | |
| 5,356,369 A | 10/1994 | Yamasaki et al. | |
| 5,360,413 A | 11/1994 | Leason et al. | |
| 5,474,544 A | 12/1995 | Lynn | |
| 5,501,426 A | 3/1996 | Atkinson et al. | |
| 5,509,433 A | 4/1996 | Paradis | |
| 5,533,708 A | 7/1996 | Atkinson et al. | |
| 5,616,130 A | 4/1997 | Mayer | |
| 5,632,735 A | 5/1997 | Wyatt et al. | |
| 5,641,184 A * | 6/1997 | Mortensen | 285/93 |
| 5,676,346 A | 10/1997 | Leinsing | |
| 5,699,821 A | 12/1997 | Paradis | |
| 5,730,418 A | 3/1998 | Feith et al. | |
| RE35,841 E * | 7/1998 | Frank et al. | 604/256 |
| 5,820,601 A | 10/1998 | Mayer | |
| 6,036,171 A | 3/2000 | Weinheimer et al. | |
| 6,039,302 A | 3/2000 | Cote et al. | |
| 6,079,432 A | 6/2000 | Paradis | |
| 6,171,287 B1 | 1/2001 | Lynn et al. | |
| 6,371,936 B1 * | 4/2002 | Heidick | 604/86 |
| 6,379,340 B1 | 4/2002 | Zinger et al. | |
| D478,662 S | 8/2003 | Flinchbaugh | |

(Continued)

OTHER PUBLICATIONS

Goodman, Eric L., "Notice of Allowance", U.S. Appl. No. 29/344,747, filed Oct. 2, 2009; mailed Dec. 1, 2011.

(Continued)

*Primary Examiner* — Aarti B Berdichevsky
*Assistant Examiner* — Bradley Osinski
(74) *Attorney, Agent, or Firm* — David S. Noskowicz; Philip H. Burrus, IV

(57) ABSTRACT

A connector (900) for fluid conduit includes a connector body (901) having a lumen (902) passing along a longitudinal axis (903), and a luer access port (800) extending distally along a transverse axis (905). The luer access port (800) is made from a thermoplastic elastomer (500) having a domed interior portion (501) and a stair-stepped perimeter (502) that is coupled to a cylindrical wall (600). The thermoplastic elastomer (500) and cylindrical wall (600) can be integrally coupled in an insert molding process.

16 Claims, 7 Drawing Sheets

(56) References Cited

U.S. PATENT DOCUMENTS

| | | | |
|---|---|---|---|
| 6,605,076 B1* | 8/2003 | Jepson et al. | 604/539 |
| D482,447 S | 11/2003 | Harding et al. | |
| 6,651,956 B2 | 11/2003 | Miller | |
| 6,991,215 B2 | 1/2006 | Kiehne | |
| 7,811,278 B2 | 10/2010 | Knipple et al. | |
| D652,510 S | 1/2012 | Lombardi et al. | |
| 2001/0054423 A1 | 12/2001 | Gray | |
| 2004/0215158 A1* | 10/2004 | Anderson | 604/327 |
| 2006/0217671 A1* | 9/2006 | Peppel | 604/246 |
| 2006/0252997 A1 | 11/2006 | Wilk | |
| 2011/0082431 A1 | 4/2011 | Burgess et al. | |
| 2012/0041391 A1 | 2/2012 | Fangrow et al. | |

OTHER PUBLICATIONS

Goodman, Eric L., "Restriction Requirement", U.S. Appl. No. 29/407,332, filed Nov. 28, 2011; mailed Mar. 2, 2012.

Goodman, Eric L., "Notice of Allowance", U.S. Appl. No. 29/407,332, filed Nov. 28, 2011; mailed Apr. 20, 2012.

* cited by examiner and out of the syringe. When the syringe is removed, the thermoplastic elastomer reseals to prevent fluid flow along the transverse axis.

CONNECTOR FOR FLUID CONDUIT WITH INTEGRATED LUER ACCESS PORT

BACKGROUND

1. Technical Field

This invention relates generally to a connector for fluid conduit, including tubing or hose, and more particularly to a connector having a port by which the luer of a syringe may take samples of fluid passing though the connector.

2. Background Art

A "luer" connector is a feature found on many syringes that facilitates a leak-free connection being made between the needle hub and a corresponding fitting. For example, a health care provider may purchase syringes and hypodermic needles separately. It is often the case that the hypodermic needle will include a female adaptor coupled thereto for mating with a syringe. This female adaptor slides over a male needle hub. To ensure that a leak-free seal is formed, a luer connector may be disposed about the needle hub. The luer connector generally looks something like a cylinder disposed about the needle hub. The luer connector may include a locking mechanism, such as threads, or may be a "slip" luer without locking mechanisms.

In fluid collection or extraction procedures, such as those involving an intravenous device or a catheter, it is often necessary to take a sample of the fluid passing through the fluid conduit, which is often rubber tubing or a similar material. This can be accomplished by coupling a hypodermic needle to a syringe and inserting the needle into the tubing to draw the sample. This process is problematic, however, in that some fluid conduit can be quite narrow, which makes it easy to pass the hypodermic needle completely through the conduit.

There is thus a need for an improved device suited for facilitating sampling of fluids from fluid conduit that is simple to manufacture, cost effective, and reliable.

Figure 1:
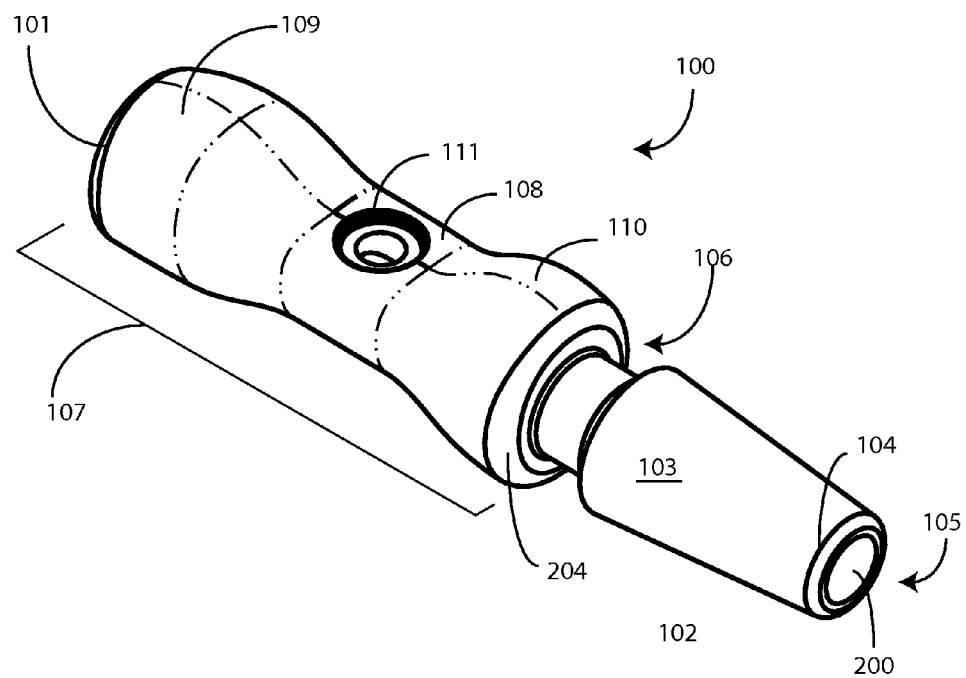
FIG. 1 illustrates a perspective view of one tubular connection member connector body in accordance with embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present invention provide a connector for fluid conduit, such as rubber tubing or other flexible conduit. The connector includes a luer access port, to which a luer connector of a needle-less syringe may couple. When the luer connector of the syringe couples to the luer access port, the needle hub of the syringe is able to pass through an aperture or opening in a thermoplastic elastomer, thereby allowing one to take a fluid sample without penetrating the fluid conduit, and without the use of a hypodermic needle.

In one embodiment, the connector includes a tubular connection member having a lumen passing therethrough. The tubular connection member includes a male conduit connector and a female receiver, which can be used for coupling the connector to conduit. The luer access port, which is a singular, insert-molded part in one embodiment, is disposed along a waist of the tubular connection member that is positioned between two higher side portions. To aid in user comfort, in one embodiment, the luer access port rises no higher from the waist than one of the side portions. To further aid in user comfort, in one embodiment the waist and side portions form a smooth contour without sharp edges.

Embodiments of the present invention facilitate fluid flow from one conduit inserted into the female receiver and another coupled about the male conduit connector through a lumen passing along a longitudinal axis of the tubular connection member. The luer access port extends from the tubular connection member along a transverse axis, which may be oriented orthogonally relative to the longitudinal axis. The thermoplastic elastomer of the luer access port ensures that fluid passes through the main lumen until either a slip luer or a lock luer is coupled to the cylindrical body of the luer access port. As the luer of the syringe connects with the luer access port, the needle hub passes through the thermoplastic elastomer, thereby permitting fluid flow along the transverse axis into the syringe. When the syringe is removed, fluid communication along the transverse axis stops.

Embodiments of the present invention offer numerous advantages over the prior art due to manufacturability. For example, while prior art luer access ports are often made with many different parts, in one embodiment of the present invention only two parts are used, as the luer access port is formed in a single mold by way of a insert molding process. This manufacturing method results in a smaller connector having a reduced form factor, as well as a lower cost connector. Size can be important in fluid connector design as connectors in accordance with the present invention are frequently used in procedures involving catheters. When used with a catheter, the connector can be placed atop the leg of the patient. If the patient rolls over on the connector, large connectors can cause irritation. Further, the smooth contours of various embodiments of the invention include no sharp edges, thereby also increasing patient comfort.

Further, embodiments of the present invention provide an access port with higher reliability when compared to prior art, multi-piece designs. Higher reliability is due at least in part to the thermoplastic elastomer being "molded into" the cylindrical wall. The insert molding process thereby reduces the opportunities for elastomer failure or the opportunities for fluid to bypass about a perimeter of the elastomer member, which results in leakage.

Other advantages embodiments of the present invention offer over prior art connectors include the following: First, in the construction of embodiments of the present invention, only two materials are needed. A first material is used for the thermoplastic elastomer, and another material is used for the cylindrical wall of the luer access port and the tubular connection member. By contrast, with prior art designs, three or more different parts are required, each of which can be manufactured from a different material.

Next, as the thermoplastic elastomer is insert molded into the cylindrical housing of the luer access port in one embodiment, the need for tediously assembling these small parts together is obviated. This results in faster manufacturing times and reduced manufacturing cost.

Third, most prior art access ports consist of a soft valve material, a rigid housing into which the valve material is glued, and a third rigid base. With embodiments of the present invention, the thermoplastic elastomer is permanently bonded into its cylindrical housing, thereby obviating the need for adhesives or solvents to contact the thermoplastic elastomer. Additionally, since the materials are bonded together, there is no need to provide large amounts of space within the luer access port for mechanical activation of the syringe valve. This results in a luer access port having a smaller overall form factor.

Figure 2:
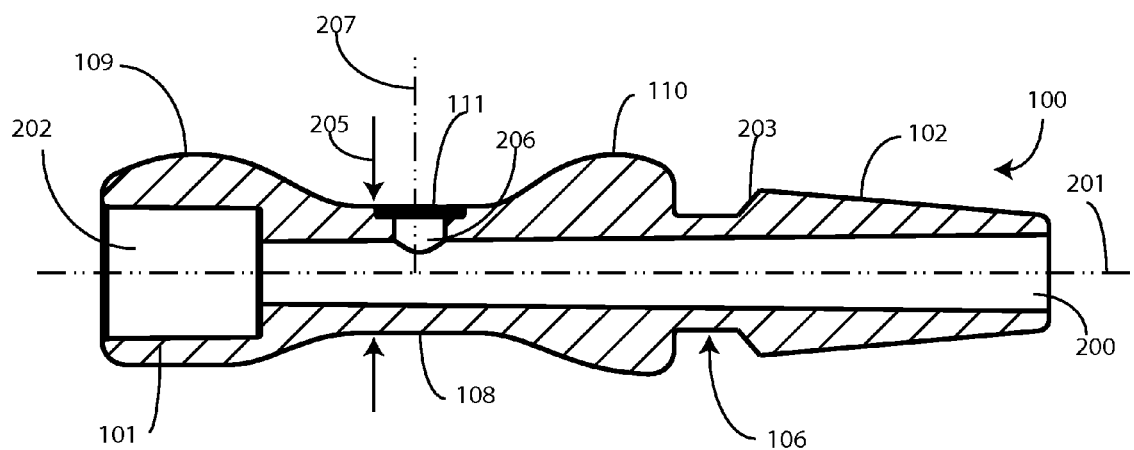
FIG. 2 illustrates a sectional view of one tubular connection member connector body in accordance with embodiments of the invention.
Figure 3:
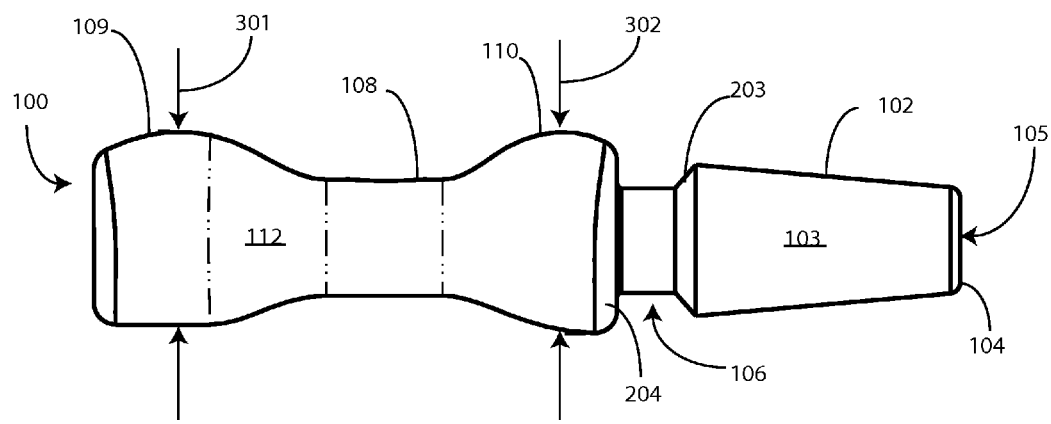
FIG. 3 illustrates a side, elevation view of one tubular connection member connector body in accordance with embodiments of the invention.
Figure 4:
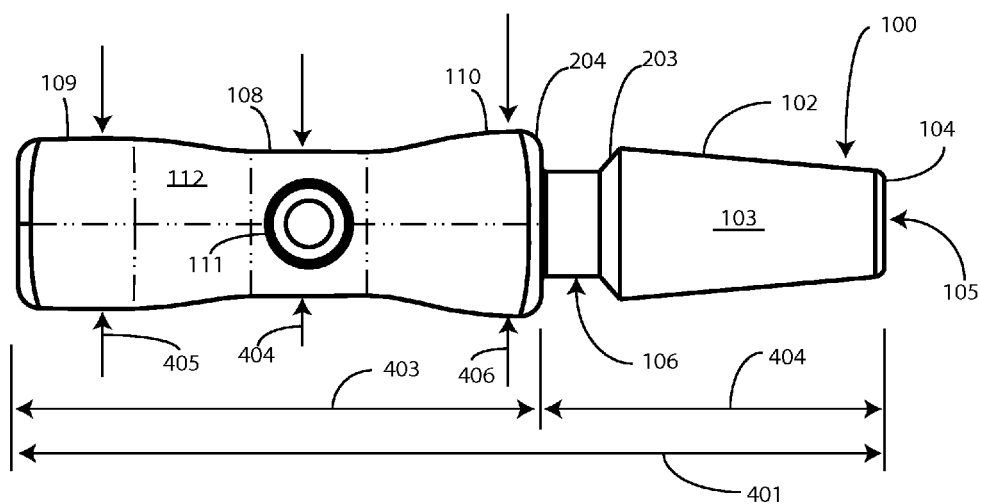
FIG. 4 illustrates a top, plan view of one tubular connection member connector body in accordance with embodiments of the invention.

Turning now to FIGS. 1-4, illustrated therein is one embodiment of a connector for a fluid conduit in accordance with embodiments of the invention. FIG. 1 illustrates a perspective view, while FIG. 2 illustrates a side, sectional view. FIG. 3 illustrates a side, elevation view, while FIG. 4 illustrates a top plan view. The figures will be referred to collectively, with like reference numerals referring to identical or functionally similar elements throughout the separate views.

A tubular connection member 101 has a lumen 200 passing therethrough. The term "tubular" refers to the fact that a lumen passes through the connection member along a longitudinal axis. Note that the term "tubular" does not mean that the tubular connection member 101 must be cylindrical, although it can be. For example, in the illustrative embodiment of FIGS. 1-4, various contours pass long the tubular connection member 101, and result in ramps, steps, and smooth contours. As such, the tubular connection member 101 is a connector body that may take any of a variety of shapes. In one illustrative embodiment, the tubular connection member 101 has a length 401 of about 3 inches, such as 2.980 inches.

Figure 13:
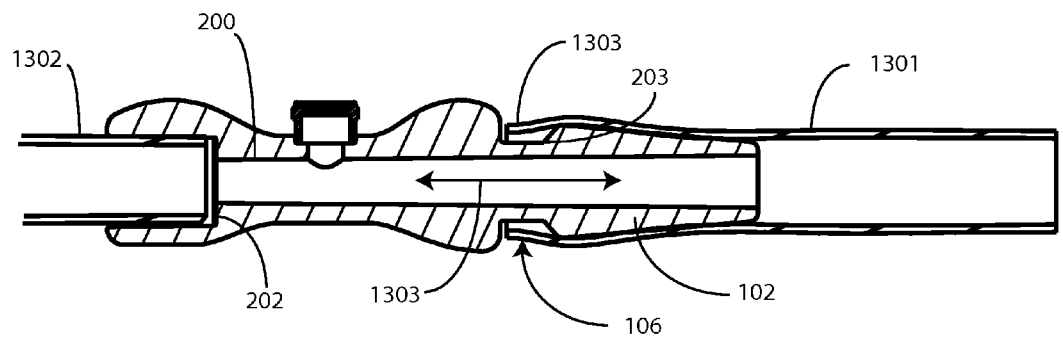
FIG. 13 illustrates one embodiment of a connector for a fluid conduit coupled to fluid conduit in accordance with one embodiment of the invention.

The lumen 200, which passes along a longitudinal axis of the tubular connection member 100 facilitates fluid communication between a male conduit connector 102 and a female conduit receiver 202. As shown in FIG. 2, in one embodiment the female conduit receiver 202 can be disposed beneath a side portion 109 of the port supporting region 107. Turning briefly to FIG. 13, the male conduit connector 102 can be inserted inside a first conduit 1301, which may be rubber or plastic tubing or other suitable conduit. A second conduit 1302 then couples within the female conduit receiver 202, thereby facilitating fluid communication between the first conduit 1301 and the second conduit 1302 through the lumen 200.

Turning now back to FIGS. 1-4, in one embodiment the male conduit connector 102 is configured as a ramp 103 extending from a steeper insertion ramp 104 disposed at a first end 105 of the tubular connection member 101, distally along the tubular connection member, to a termination ramp 203. An optional sleeve 106 is disposed behind the termination ramp 203, which extends from the termination ramp 203 to a walled stop 204. The length 402 of the combined insertion ramp 104, ramp 103, termination ramp 203, and sleeve 106, in one embodiment, is about 1.180 inches.

As shown in FIG. 13, when a first conduit 1301 is slipped over the male conduit connector 102, the end 1303 of the first conduit 1301 may slip into the sleeve 106. As such, the termination ramp 203 serves as a stop to retain the first conduit on the male conduit connector 102. Further, the walled stop 204 helps to prevent the first conduit 1301 from sliding too far along the tubular connection member 101.

Turning back to FIGS. 1-4, beyond the sleeve 106 is disposed a port support region 107 comprising a waist 108 disposed between two side portions 109,110. As shown in the illustrative embodiment of FIGS. 1-4, in one embodiment each of the two side portions 109,110 is has a height 301,302 that is greater then a waist height 205. For example, a first side portion height 301 may be 0.664 inches, while a second side portion height 302 is 0.692 inches. The waist height 205 may only be 0.400 inches. The length 403 of the port support region 107, in one embodiment, is about 1.800 inches. These values are illustrative only, in that one of ordinary skill in the art having the benefit of this disclosure will find it obvious that other dimensions have been used. However, these dimensions have been shown in experimental testing to work well in practice.

As shown in the illustrative embodiment of FIGS. 1-4, the port support region 107 has a cross sectional shape that is non-cylindrical. In the illustrative embodiments of FIGS. 1-4, the port support region 107 has an hourglass or "pinched cigarette butt" appearance as the port support region 107 tapers from a first side portion 109 to the waist 108 to the second side portion 110. Note that in the illustrative embodiments of FIGS. 1-4, the waist 108, first side portion 109, and second side portion 110 have widths 404,405,406 that are different from their respective heights 301,302,205. For example, while the waist 108 may have a waist height 205 of 0.400 inches, its width 404 may be 0.498 inches. Similarly, while the first side portion 109 may have a height of 0.664 inches, its width 405 may be only 0.581 inches. Accordingly, while the second side portion 110 may have a height of 0.692 inches, its width 406 may only be 0.638 inches. The widths and heights of the port support region 107 could be the same as well.

As noted above, in some applications the connector 100 will be used in a catheter process in which the connector 100 is placed along, or very near to, a person's leg or arm. As such, a person can roll onto the connector 100 at times. To aid in user comfort, as shown in FIGS. 1-4, in one embodiment the surface area 112 defining the contours flowing along the port support region 107 are smooth and are devoid of corners or sharp edges.

Disposed along the waist 108 is a port receiving aperture 111. The port receiving aperture 111 includes its own lumen 206 that is disposed about a transverse axis 207. In one embodiment, the transverse axis 207 is orthogonal with the longitudinal axis 201, although other angles can be used as well. The port receiving aperture 111 is configured to couple to the access port that will be described with respect to the figures below.

Figure 5:
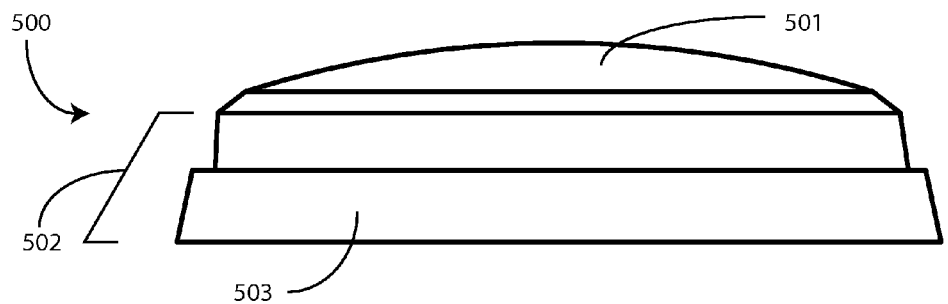
FIG. 5 illustrates a perspective view of a thermoplastic elastomer in accordance with embodiments of the invention.

Turning now to FIG. 5, illustrated therein is one embodiment of a thermoplastic elastomer 500 suitable for use with embodiments of the invention. While the thermoplastic elastomer 500 is shown as an independent element in FIG. 5, as will be described below it can be integrated into a cylindrical wall in an insert molding process. Where this is the case, the cylindrical wall and thermoplastic elastomer 500 will be removed from the mold in a single piece. The illustration of the thermoplastic elastomer 500 shown in FIG. 5 is used to show some features and characteristics of one exemplary embodiment.

As shown in FIG. 5, the thermoplastic elastomer 500 includes a domed interior portion 501 surrounded by a stair-stepped perimeter portion 502. In this illustrative embodiment, the stair-stepped perimeter portion 502 includes two steps, although those of ordinary skill in the art having the benefit of this disclosure will understand that other numbers of steps can be used. The steps serve to provide additional surface area to which the cylindrical sidewall can adhere. Further the lower step 503 of the thermoplastic elastomer 500 may be integrated into the cylindrical sidewall, thereby leaving the domed interior portion 501 free to move. In one embodiment, the thermoplastic elastomer 500 is manufactured from a flexible, resilient material having both thermoplastic and elastomeric properties. One suitable material shown to work well in practice is Versaflex® OM 9-802CL offered by GLS Corporation. This material is clear and readily combines with polycarbonate resins in insert molding processes.

Figure 6:
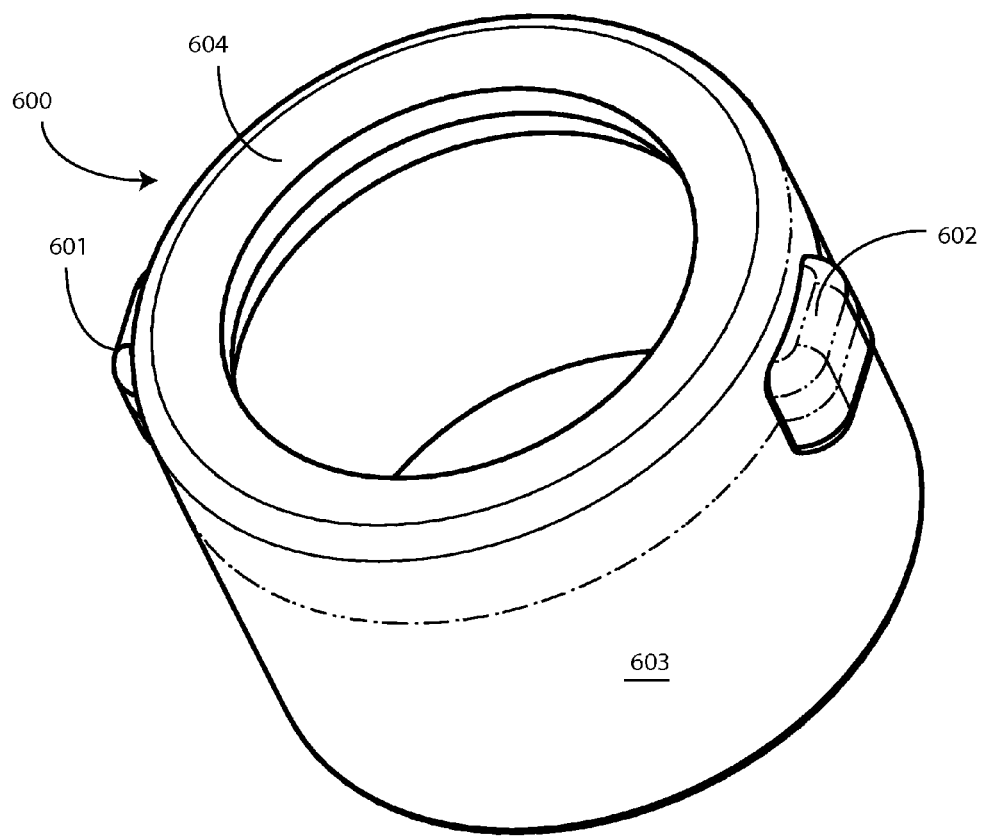
FIG. 6 illustrates a perspective view of a luer port cylindrical wall in accordance with embodiments of the invention.

Turning now to FIG. 6, illustrated therein is one embodiment of a cylindrical wall 600 that is formed about the thermoplastic elastomer (500) of FIG. 5. As with the thermoplastic elastomer (500) of FIG. 5, the cylindrical wall is shown as an independent element in FIG. 6. However, as will be described below, it can be integrated about the thermoplastic elastomer (500) in an insert molding process. Where this is the case, the cylindrical wall 600 and thermoplastic elastomer (500) will be removed from the mold in a single piece. The illustration of the cylindrical wall shown in FIG. 6 is used to show some features and characteristics of one exemplary embodiment.

In one embodiment, the cylindrical wall 600 is configured as a cylinder such that it will easily slip between a luer connector and needle hub of a syringe. The cylindrical wall 600 can be manufactured from a rigid thermoplastic, such as ABS, polycarbonate, polycarbonate-ABS, and so forth. In one embodiment, polycarbonate is used for the cylindrical wall 600 due to the fact that it easily bonds with polyvinyl chloride materials with commonly available solvents such as cyclohexanone or methylene chloride.

The cylindrical wall 600 can be configured to couple with slip luer connections or locking luer connections. Where the cylindrical wall 600 is configured to couple to a locking luer connection, in one embodiment, the cylindrical wall 600 includes one or more male engagement members 601,602 extending therefrom. These male engagement members 601, 602 are configured to engage the locking mechanism of a locking luer connector, which may be in the form of threads, twist snaps, or other mechanical configurations. Where the cylindrical wall 600 is configured to couple to slip luer connectors, the male engagement member 601,602 may be omitted. However, a cylindrical wall 600 having male engagement member 601,602 that only slightly protrude from the perimeter wall 603 so as to either engage the locking mechanism of a locking luer connector, or to slide within a slip luer connector.

In one embodiment, the cylindrical wall 600 includes a terminating ledge 604 that is complementary in shape to the stair-stepped perimeter (502) of the thermoplastic elastomer (500). During the insert molding process, the terminating ledge 604 fuses with the stair-stepped perimeter (502), thereby forming a unitary luer access port.

Figure 7:
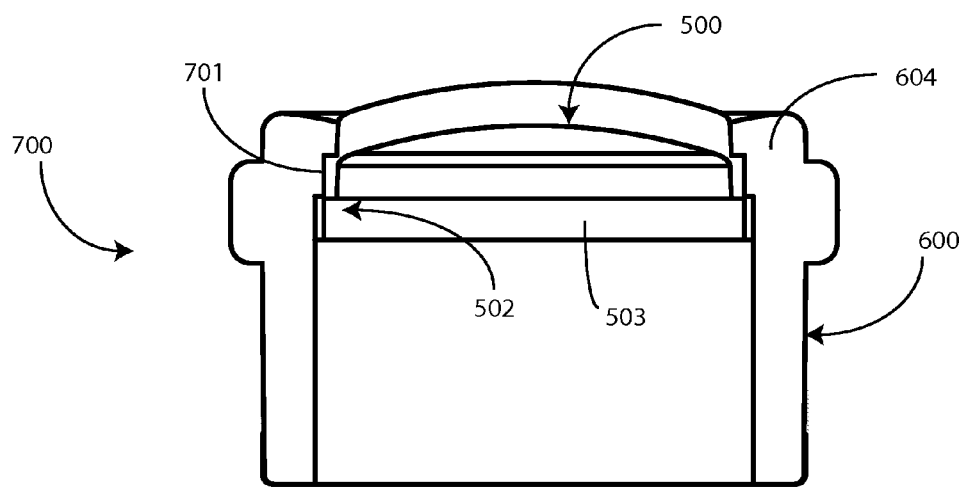
FIG. 7 illustrates a sectional view of a luer port in accordance with embodiments of the invention.

Turning now to FIG. 7, illustrated therein is one embodiment of a unitary luer access port 700, shown in a sectional view, comprising a thermoplastic elastomer 500 and a cylindrical wall 600. The unitary luer access port 700 of FIG. 7 has been formed with an insert molding process, where the stair-stepped perimeter 502 mates with a complementary stair-stepped feature 701 inside the terminating ledge 604. In one embodiment, the port height 702 is less than 0.200 inches.

Figure 8:
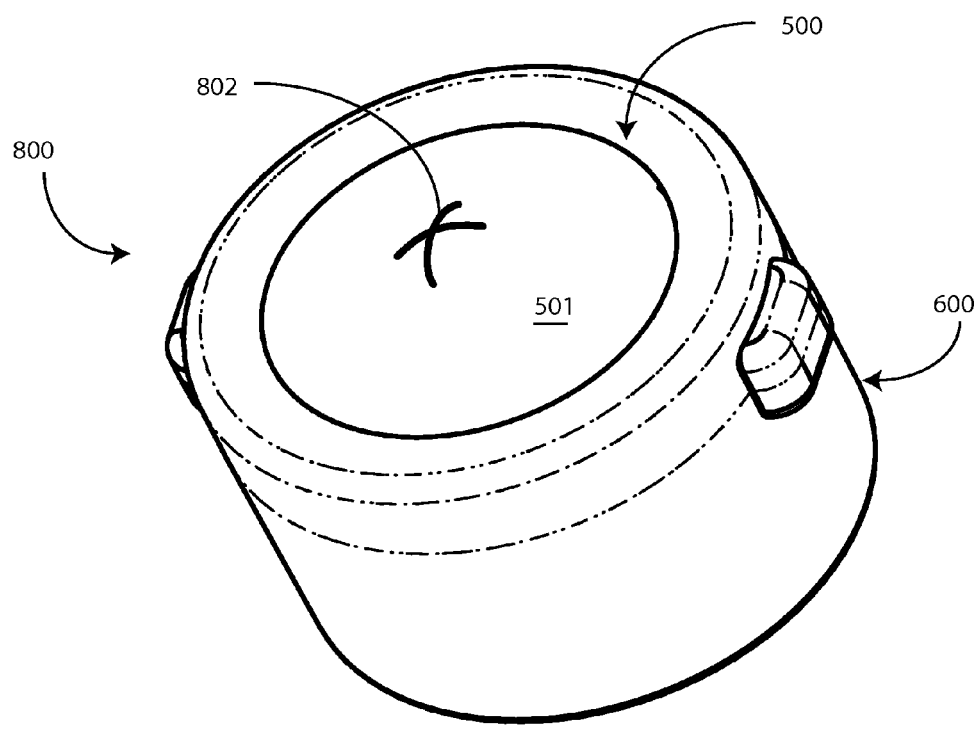
FIG. 8 illustrates a perspective view of a luer port with a slit thermoplastic elastomer in accordance with embodiments of the invention.

Turning now to FIG. 8, illustrated therein is another embodiment of a luer access port 800 in accordance with embodiments of the invention. In the embodiment of FIG. 8, the domed interior portion 501 of the thermoplastic elastomer 500 has been cut so as to reveal an incision 802 spanning a length of the domed interior portion 501. Note that the length is not the diameter, but is rather a portion of the domed interior portion 501. The incision 802 defines an aperture that is configured such that a needle hub of a needle-less syringe may pass through the aperture so as to draw fluid samples through the luer access port 800. As thermoplastic elastomer 500 has elastomeric properties, when the needle hub is withdrawn, the incision 802 closes, thereby stopping fluid communication through the luer access port 800.

In one embodiment, the incision 802 is large enough for the needle hub to fully pass therethrough. However, in one embodiment the incision 802 is not large enough to extend across the entire width of the domed interior portion 501, as this can compromise reliability of the bond between the thermoplastic elastomer 500 with the cylindrical wall 600.

In one embodiment, the function of the luer access port 800 is to establish fluid communication from a syringe to the lumen of a flow channel in a connector body or tubular connection member. When there is not a needle hub inserted into the luer access port 800, no fluid is allowed through the thermoplastic elastomer 500. When a needle hub is inserted into the luer access port 800, the thermoplastic elastomer 500 stretches and displaces, thereby allowing the needle hub to pass through the incision 802 and establish fluid communication with internal lumen of the connector body or tubular connection member. To draw a sample of fluid, the healthcare provider need only insert the needle hub through the incision 802, thereby causing the luer connector to pass about the cylindrical wall 600. The healthcare provider can then aspirate the syringe and draw a sample of fluid. The thermoplastic elastomer 500 material is chosen so that it is soft enough to allow the needle hub to pass though without resistance. The thermoplastic elastomer 500 material is also chosen so that it is resilient and can close quickly upon removal of the needle hub to ensure the prevention of leaks.

Figure 9:
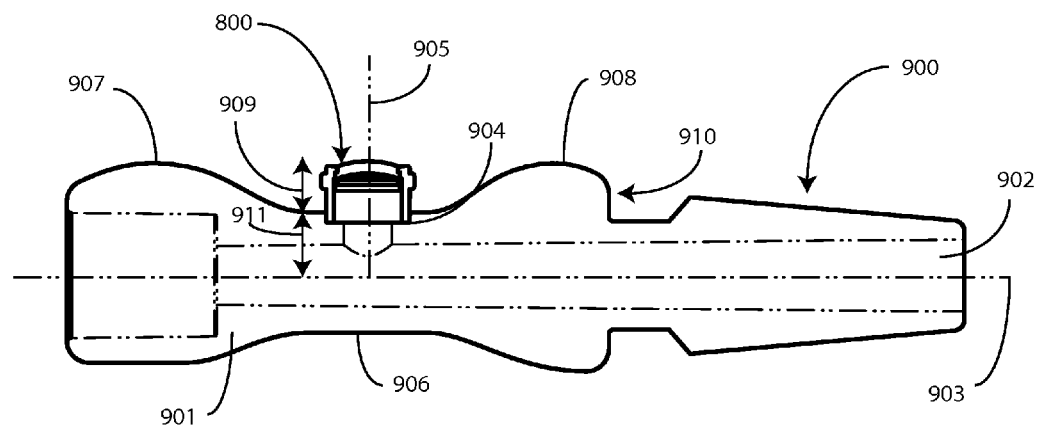
FIG. 9 illustrates a sectional view of a connection member having a luer port coupled thereto in accordance with embodiments of the invention.
Figure 10:
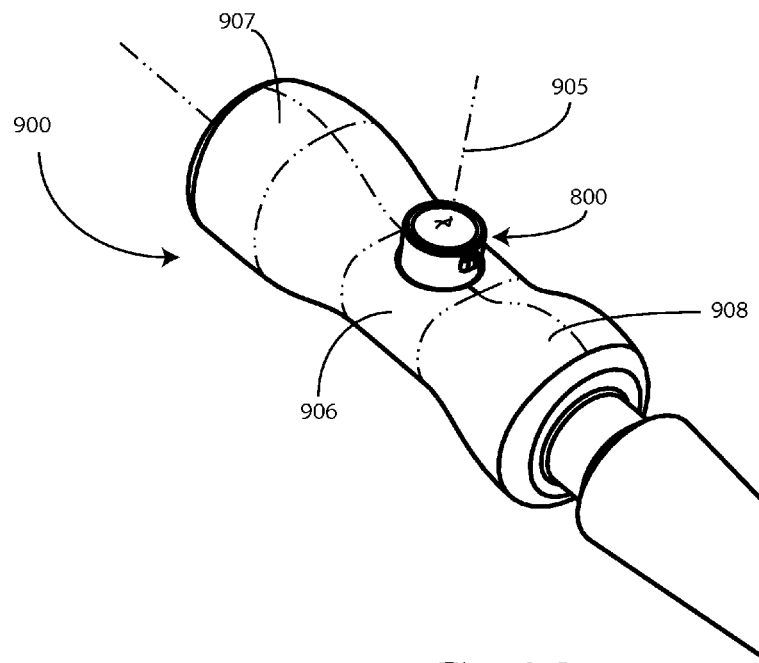
FIG. 10 illustrates a perspective view of a connection member having a luer port coupled thereto in accordance with embodiments of the invention.

FIGS. 9 and 10, illustrated therein is one embodiment of a connector 900 for a fluid conduit in accordance with embodiments of the invention. The fluid connector 900 of FIGS. 9 and 10 includes a connector body 901 having a main lumen 902 passing therethrough along a longitudinal axis 903. The connector body 901, in this illustrative embodiment, is configured just as was the tubular connection member (101) of FIGS. 1-4, with a port receiving aperture 904 to which a luer access port 800 is coupled. In one embodiment, the luer access port 800 is coupled to the port receiving aperture 904 at the waist 905 of the connector body 901, which is disposed between two side sections 907,908. In one embodiment, the luer access port 800 is coupled to the port receiving aperture 904 of the connector body 901 with adhesives. In another embodiment, the luer access port 800 can be threaded into the port receiving aperture 904. In another embodiment, the luer access port 800 can be sonically or thermally welded into the port receiving aperture 904.

Regardless of the means of connecting, in the illustrative embodiment of FIGS. 9 and 10, the luer access port 800 extends distally along a transverse axis 905 from a waist 906 of the connector body 901 that is disposed between two side sections 907,908. In FIG. 9, the luer access port 800 has a height 909 that is configured such that the luer access port 800 extends from the connector body 901 to a height that is less than a side section height 910 of the highest of the two side sections 907,908. In so doing, the configuration of the connector 900 aids in user comfort in that the luer access port 800 is not the highest feature. As such, the combination of both side sections 907,908 and the luer access port 800 form a three-element surface that will not substantially irritate a user if the user rolls over the connector 900.

In one embodiment, the height 910 of the highest of the two side portions 907,908 is greater than or equal to a waist height 911 of the waist 906 plus the port height 909. For example, where a height 910 of the higher side portion 908 is 0.400 inches, the waist height 911 can be less than 0.200 inches and the port height 909 can be less than 0.200 inches. In another embodiment, the height may be 0.346 inches, while the waist height 911 is 0.200 inches. In this configuration, the port height 909 will be less than or equal to 0.146 inches.

Figure 11:
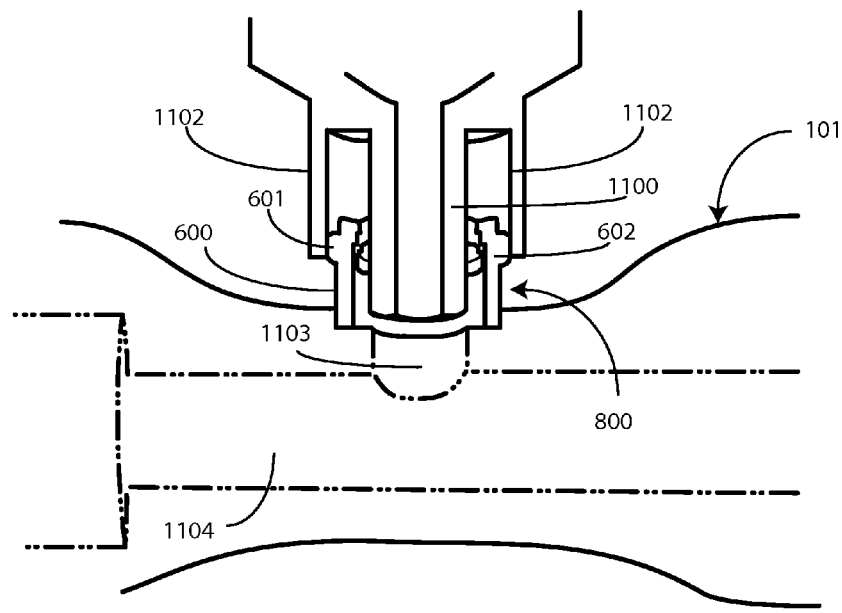
FIG. 11 illustrates a needle-less syringe with a needle hub passing through an aperture in a thermoplastic elastomer.

Turning now to FIG. 11, illustrated therein is a needle hub 1100 of a needle-less syringe being inserted into one embodiment of a luer access port 800 coupled to a tubular connection member 101 in accordance with embodiments of the invention. The syringe of FIG. 11 is a slip luer syringe, as the luer connector 1102 does not include any luer locking members. Note that even though the syringe is a slip luer syringe, the cylindrical wall 600 still includes male engagement members 601,602. However, each male engagement member 601,602 extends from the cylindrical wall 600 sufficiently little as to fit within the luer connector 1102.

As shown in the sectional view of FIG. 11, the needle hub 1100 passes through the incision (802) of the thermoplastic elastomer 500. The needle hub 1100 thus enters the lumen 1103 of the luer access port 800, thereby facilitating withdrawal of fluids from the main lumen 1104 passing through the tubular connecting member 101.

Figure 12:
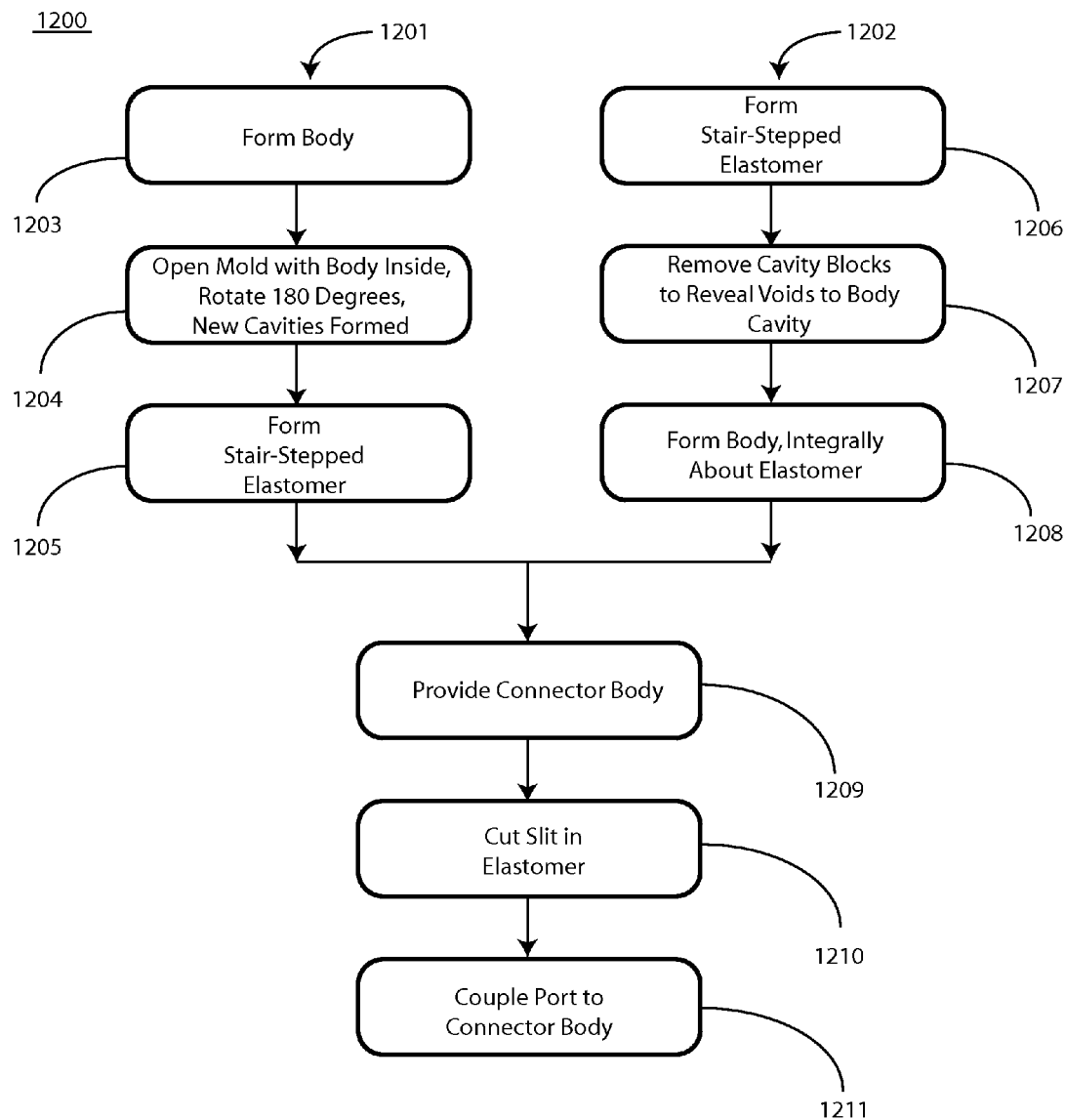
FIG. 12 illustrates one method for manufacturing a connector having a luer port in accordance with embodiments of the invention.

Turning now to FIG. 12, illustrated therein are exemplary methods 1200 for manufacturing a luer access port and a corresponding connector for fluid conduit with an insert molding process in accordance with embodiments of the invention. As shown in FIG. 2, flow 1201 is one exemplary method of forming a luer access port, while flow 1202 is another. It will be obvious to those of ordinary skill in the art having the benefit of this disclosure that other insert molding process flows for creating a luer access port can be used.

Generally, the method includes the following steps: forming a first portion of the luer access port in a mold by injecting a first material into a cavity of the mold as shown by steps 1203 and 1206; removing at least one tooling component from the cavity, thereby creating additional cavity space as shown by steps 1204 and 10207; and forming a second portion of the luer access port by injecting a second material into the cavity about the stair-stepped elastomer membrane to form the luer access port as shown at steps 1205 and 1208. Where the stair-stepped elastomer is formed first, the first material injected into the mold will be elastomer, and the second material will be a thermoplastic like polycarbonate. When the luer access port body is formed first, the first material will be a thermoplastic, while the second material will be an elastomer.

In one embodiment, this process can be carried out using a mold having two sets of cores and cavities, where the cores are the same, but the cavities are different from each other. As such, the stair-stepped elastomer and luer access port body can be constructed at the same time, thereby increasing efficiency of manufacture. Once the luer access port is formed, regardless of method, it can then be coupled to a connector at step 1209.

Flow 1201 describes a process in which the luer access port body is formed first. At step 1203, the luer access port body is formed by injecting a first material, such as a thermoplastic like polycarbonate, into an injection mold cavity. At step 1204, the mold can opened with the luer access port body still within the mold, thereby forming new cavities. The mold can then rotated 180 degrees out of phase so that the injection equipment is facing the additional cavities. At step 1205, a separate injection unit of the injection equipment can then inject a second material, such as an elastomer, into the new cavities such that it forms with the luer access port body. This step 1205 completes the formation of a unitary, integrated luer access port.

At step 1209, a connector body is provided. The connector body, as described with respect to the embodiments above, includes a first lumen extending along a longitudinal axis and a second lumen extending along a transverse axis and intersecting the first lumen. At step 1210, an incision or slit is formed in the stair-stepped elastomer membrane so as to facilitate passage of a needle hub therethrough. At step 1210, the unitary, integrated access port is coupled to the connector body about the transverse axis as described above. The resulting connector can then be used or shipped to healthcare providers for use.

Turning now to flow 1202, in this flow the stair-stepped elastomer is formed first. Specifically, at step 1206, a stair-stepped elastomer membrane is formed in a mold by injecting elastomer material into a first cavity of the mold. The first cavity, which is for the stair-stepped elastomer membrane, is blocked from a second cavity for the body cores within the mold.

At step 1207, at least one tooling component, such as a core, is removed from the mold, thereby increasing a cavity size of the mold and providing exposure of the now formed stair-stepped elastomer membrane to the second cavity for the body. At step 1208, a body of a luer access port is formed by injecting thermoplastic material into the second cavity that has been exposed about the stair-stepped elastomer membrane. This step 1208 completes the formation of a unitary, integrated luer access port. The luer access port can then be formed into a connector at steps 1209, 1210, and 1211, as described above.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. An access port for a connector configured to couple to fluid conduit, the access port comprising a thermoplastic elastomer insert molded into a cylindrical wall, the access port coupled to a waist of a tubular connection member disposed between two side portions, the waist and the two side portions defining a port support region with an hourglass appearance, the two side portions each having a height greater than the waist, the height of a highest of the two side portions greater or equal to a waist height of the waist, plus a port height of the access port.

2. The access port of claim 1, wherein the thermoplastic elastomer comprises a domed interior portion surrounded by a stair-stepped perimeter portion.

3. The access port of claim 2, wherein the domed interior portion comprises an incision aperture spanning a length of the domed interior portion.

4. The access port of claim 1, the tubular connection member having a lumen passing therethrough and comprising a male conduit connector and a female conduit receiver, the two side portions each having a height greater than the waist.

5. The access port of claim 4, wherein one or more of the waist and the two side portions has a cross-sectional shape that is non-cylindrical.

6. The access port of claim 5, wherein the waist has a waist width that is greater than a waist height.

7. The access port of claim 6, wherein the waist width is less than or equal to 0.250 inches, the waist height is less than or equal to 0.200 inches, and a port height is less than or equal to 0.200 inches.

8. The access port of claim 4, wherein a surface area spanning the waist and the two side portions is smooth.

9. The access port of claim 4, the tubular connection member a male conduit connector and a collar disposed between a first side portion and the male conduit connector.

10. The access port of claim 1, wherein the cylindrical wall comprises one or more male engagement members extending therefrom, wherein the one or more male engagement members are configured to engage a locking luer of a syringe.

11. A connector for fluid conduit, comprising a connector body having a main lumen passing along a longitudinal axis, the connector body comprising a luer access port extending distally along a transverse axis from a waist of the connector body disposed between two side sections, the waist and the two side sections defining a contour devoid of edges, the waist having a height less than the two side sections, wherein the luer access port has a port height such that a sum of the height and the port height is less than a side section height of a highest of the two side sections.

12. The connector of claim 11, wherein the luer access port comprises a thermoplastic elastomer that is insert molded into a cylindrical wall.

13. The connector of claim 12, wherein the thermoplastic elastomer defines an aperture configured such that a needle hub of a needle-less syringe may pass through the aperture.

14. The connector of claim 11, the contour devoid of corners.

15. The connector of claim 14, wherein the connector body further comprises a female conduit engagement member disposed about the longitudinal axis and beneath at least one of the two side sections.

16. The connector of claim 11, wherein the connector body comprises a male conduit engagement member disposed about the longitudinal axis and separated from one of the two side sections by a collar.

* * * * *